United States Patent [19]

Tóth et al.

[11] Patent Number: 4,618,611

[45] Date of Patent: Oct. 21, 1986

[54] 1-(AMINOALKOXYPHENYL)-1-PHENYL-PROPANOLS, PROCESS FOR THEIR PREPARATION AND PHARMACEUTICAL COMPOSITIONS CONTAINING THEM

[75] Inventors: Edit Tóth; József Törley; György Fekete; László Szporny; László Vereczkey; Éva Pálosi; Imre Klebovich; Pál Vittay; Sándor Görög; István Hajdu, all of Budapest, Hungary

[73] Assignee: Richter Gedeon Vegyeszeti Gyar Rt, Budapest, Hungary

[21] Appl. No.: 565,901

[22] Filed: Dec. 27, 1983

[30] Foreign Application Priority Data

Dec. 28, 1982 [HU] Hungary .............................. 4190/82

[51] Int. Cl.[4] ................. A61K 31/495; C07D 295/02; C07C 149/32
[52] U.S. Cl. ................................... 514/255; 544/396; 544/397; 564/324
[58] Field of Search .................. 564/324; 260/581.18; 424/316, 330; 544/396, 397; 514/545, 648, 255

[56] References Cited

U.S. PATENT DOCUMENTS 3,494,961  2/1970  Ruegg et al. ................... 564/324 X
4,094,908  6/1978  Toth et al. ........................ 564/324

Primary Examiner—Robert V. Hines
Attorney, Agent, or Firm—Karl F. Ross; Herbert Dubno

[57] ABSTRACT

The invention relates to new aminopropanol derivatives of the formula (I)

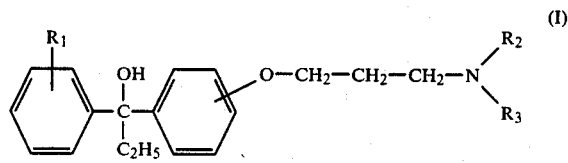

wherein
$R_1$ is halogen, trihalomethyl, alkoxy having from one to 3 carbon atoms or alkyl having from one to 3 carbon atoms,
$R_2$ is alkyl having from one to 3 carbon atoms, and
$R_3$ is cycloalkyl having from 3 to 6 carbon atoms, or
$R_2$ and $R_3$ together with the nitrogen they are attached to form an up to 8 membered ring optionally containing oxygen or a further nitrogen as an additional hetero atom, and optionally substituted with alkyl having from one to 4 carbon atoms or benzyl, and acid addition and quaternary ammonium salts thereof.

According to another aspect of the invention there are provided processes for the preparation of these compounds.

The new compounds are suitable for the treatment of acute ethanolic intoxication. Pharmaceutical compositions containing them are also within the scope of the invention.

5 Claims, No Drawings

1-(AMINOALKOXYPHENYL)-1-PHENYL-PROPANOLS, PROCESS FOR THEIR PREPARATION AND PHARMACEUTICAL COMPOSITIONS CONTAINING THEM

SPECIFICATION

This invention relates to new aminopropanol derivatives and acid addition and quaternary ammonium salts thereof. More particularly, the invention concerns new 1-(aminoalkoxyphenyl)-1-phenyl-propanols of the formula (I)

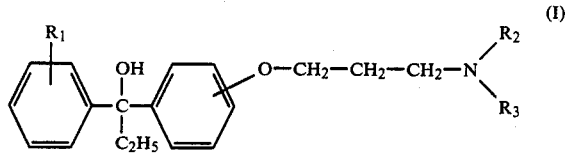

wherein $R_1$ is halogen, trihalomethyl, alkoxy having from one to 3 carbon atoms or alkyl having from one to 3 carbon atoms, $R_2$ is alkyl having from one to 3 carbon atoms, and $R_3$ is cycloalkyl having from 3 to 6 carbon atoms, or $R_2$ and $R_3$ together with the nitrogen to which they are attached to form an up to 8 membered ring optionally containing an oxygen or a further nitrogen atom as an additional hetero atom, and optionally substituted with alkyl having from one to 4 carbon atoms or benzyl, and acid addition and quaternary ammonium salts thereof. The invention further relates to a process for the preparation of these compounds and pharmaceutical compositions containing them as active ingredient.

The term "halogen" as used herein embraces all of the halogens, and may be fluorine, chlorine, bromine or iodine, preferably fluorine or chlorine.

The trihalomethyl groups may contain any of the halogens listed above but fluorine is preferred.

The term "alkoxy having from one to 3 carbon atoms" is used herein to refer to straight or branched chained alkoxy groups containing from one to 3 carbon atoms, preferably methoxy.

The term "alkyl having from one to 3 carbon atoms" refers to straight or branched chained aliphatic hydrocarbon groups containing from one to 3 carbon atoms, i.e. methyl, ethyl, n- or i-propyl.

The cycloalkyl groups are cyclic hydrocarbon groups containing from 3 to 6 carbon atoms.

Preferred representatives of the heterocyclic rings formed by the attachment of $R_2$ and $R_3$ include morpholino, piperazino and imidazolo rings.

Compounds of analogous structure are disclosed for example in the following references: C.A. 22, 410[1]; 35, 1781[2]; 40, 4712[5]; 42, P 1015 b; 47, 9548 e; 50, 12390 c; 50, 2509 i; 55, 17915 e; 55, 15413 b; 75, 103682 b; 76, P 119921 k; 82, 16477 g; 90, 86082 g; 92, 52927 b. None of these citations does, however, mention any pharmaceutical activity of the disclosed compounds.

According to a further aspect of the present invention there is provided a process for the preparation of the compounds of the formula (I), wherein $R_1$, $R_2$ and $R_3$ each have the same meanings as defined above, which process comprises (a) reacting a propiophenone of the formula (II)

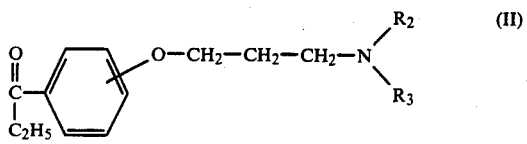

wherein $R_2$ and $R_3$ are as defined above, with an organometallic compound of the formula (III)

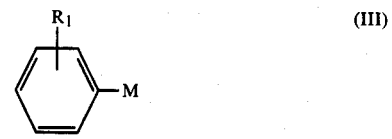

wherein $R_1$ is as defined above, and

M represents an alkali metal, preferably lithium, potassium or sodium, or an MgX group, in which X is halogen; or (b) reacting a compound of the formula (IV)

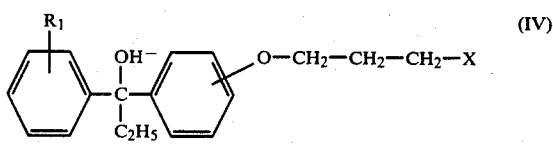

wherein $R_1$ is as defined above, and X is halogen, with a secondary amine of the formula (V)

wherein $R_2$ and $R_3$ are as defined above, preferably in the presence of an acid binding agent; or (c) reacting a benzophenone of the formula (VI)

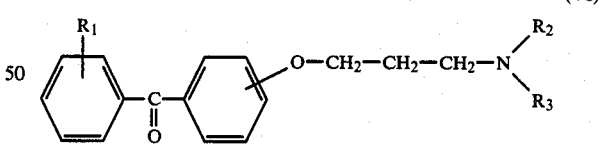

wherein $R_1$, $R_2$ and $R_3$ each have the same meanings as defined above, with an organometallic compound containing an ethyl group, preferably an ethyl magnesium halide or ethyl lithium; or (d) reacting a propiophenone of the formula (VII)

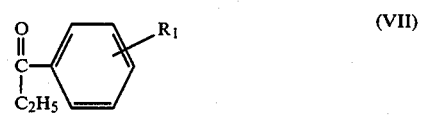

wherein $R_1$ is as defined above, with a Grignard compound of the formula (VIII)

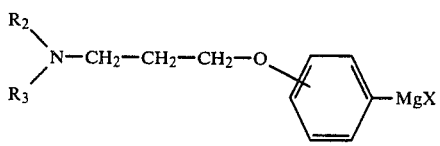

wherein $R_2$ and $R_3$ are as defined above, and X is halogen; or (e) reacting a compound of the formula (IX)

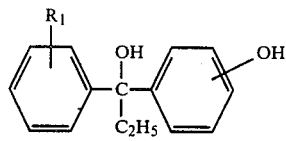

wherein $R_1$ is as defined above, preferably in the form of an alkali metal or quaternary ammonium phenolate thereof, with a tertiary amine of the formula (X)

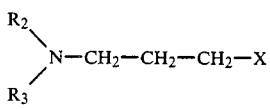

wherein $R_2$ and $R_3$ are as defined above, and X is alkylsulfonyloxy, arylsulfonyloxy or halogen, or a salt thereof, preferably in the presence of an acid binding agent, and if desired, converting any of the products obtained by process variants (a) to (e) into their acid addition or quaternary ammonium salts, or converting a product obtained as an acid addition salt into a corresponding free base and/or converting a free base into an acid addition or quaternary ammonium salt thereof.

The starting compounds are known or can be prepared by methods known in the art. The ketones of the formulae (II), (VI) and (VII) can for example be synthetized by Friedel-Crafts ketone synthesis (G. A. Olah: Friedel-Crafts and Related Reactions, III/1, Ed., Interscience Publishers (1964) 1–63).

The compounds of the formulae (III) and (VIII) can for example be prepared by preparing Grignard reactants from the corresponding substituted aryl halides in a known manner (M. S. Kharash et al.: Grignard Reactions of Nonmetallic Substances, Ed., Prentice-Hall. Inc. (1954) 5–90), while the alkali metal-organic compounds can for example be obtained following the method disclosed in Houben-Weyl: Methoden der Organischen Chemie, XIII/1, 134–159; 389–405 (1970).

Compounds of the formulae (IV) and (IX) can for example be synthesized by reacting the corresponding propiophenones with Grignard reactants in a known manner (see e.g. M. S. Kharash et al.: Grignard Reactions of Nonmetallic Substances, Ed., Prentice-Hall Inc., (1954) 138–143).

According to a preferred embodiment of process variant (a) a propiophenone of the formula (II) is reacted with an organometallic compound of the formula (III) in a dry inert organic solvent. As a compound of the formula (III) preferably the corresponding substituted phenyl magnesium chloride or bromide or the corresponding substituted phenyl lithium is used. The reaction is preferably carried out in an aprotic organic solvent, e.g. in an aliphatic ether such as diethyl either, di-n-butyl ether or diethylene glycol dimethyl ether, an alicyclic ether such as tetrahydrofuran, dioxane, an aliphatic or aromatic hydrocarbon as ligroin, benzene, toluene, xylene, dimethyl sulfoxide or hexamethyl phosphorus amide, or a mixture of these solvents. The organometallic compound is used in an at least equimolar amount. The reaction is preferably performed in an inert gas atmosphere, e.g. in nitrogen or argon. The reaction temperature may range from $-60°$ C. up to the boiling point of the solvent, and preferably is between $-30°$ C. and $100°$ C. When the reaction is complete, the reaction mixture is decomposed, preferably with an aqueous solution of ammonium chloride, and the obtained compound of the formula (I) is separated. The product can be purified by known techniques, e.g. by distillation or crystallization.

According to process variant (b) a compound of the formula (IV), in which X preferably represents chlorine or bromine, is reacted with a secondary amine of the formula (V). The reaction is preferably carried out in an organic solvent, in the presence of a base suitable for binding the acid formed in the reaction.

As a solvent for example hydrocarbons such as ligroin, benzene, toluene, halogenated hydrocarbons such as chloroform, ethers such as dioxane, alcohols such as ethanol, esters such as ethyl acetate, acid amids such as dimethyl formamide, ketones such as acetone, methyl isobutyl ketone, and mixtures of these solvents are employed. Suitable acid binding agents include inorganic and tertiary organic bases but the excess of an amine of the formula (V) may equally be used for this purpose. If the excess of the amine of the formula (V) or a tertiary organic base is used to bind the hydrogen halide formed in the course of the reaction, these may well serve as a solvent, too. The reaction is carried out at a temperature between $20°$ C. and the boiling point of the solvent. After termination of the reaction the product is isolated, e.g. by pouring the reaction mixture onto water, and separating the product by solvent extraction. The organic phase is washed to halogen-free with water, dried and evaporated. The crude product can be purified for instance by distillation or crystallization.

According to process variant (c) a benzophenone of the formula (VI) is preferably reacted with an at least equimolar amount of ethyl magnesium bromide or ethyl magnesium iodide or ethyl lithium. The reaction is accomplished in an inert dry organic solvent, essentially as described in connection with process variant (a).

According to process variant (d) the Grignard compounds of the formula (VIII), in particular those in which represents bromine, are reacted with an at least equimolar amount of a propiophenone of the formula (VII), in an anhydrous inert organic solvent, similarly to process variant (a).

According to a preferred embodiment of process variant (e) compounds of the formula (IX), preferably in form of their alkali metal or quaternary ammonium phenolates, are condensed with the tertiary amines of the formula (X). As a tertiary amine for example mesylate, tosylate bromide or preferably chloride is employed as a free base or a salt, e.g. hydrogen halide thereof. The reaction is preferably carried out in an inert organic solvent, in the presence of an acid binding agent, under anhydrous conditions or in a mixture of water and an organic solvent. As organic solvents for example esters such as ethyl acetate, ethers such as tetrahydrofuran or diethyl ether, hydrocarbons such as ligroin, benzene, toluene or xylene, halogenated hydrocarbons such as chloroform, chlorobenzene, acid amides such as dimethyl formamide, ketones such as acetone, methyl ethyl ketone or methyl isobutyl ketone, alcohols such as ethanol, propanol, etc. are used. Compounds of the formula (IX) can be converted into their phenolates by methods known in the art, e.g. with alkali metal alcoholates, amides, hydrides, hydroxides, carbonates of quaternary ammonium compounds. Preferred acid binding agents include inorganic and tertiary organic bases, e.g. sodium hydroxide, potassium hydroxide, potassium carbonate, triethyl amine, pyridine, etc. The reaction is optionally performed in the presence of a catalyst. As a catalyst for example alkali metal halides, preferably alkali metal iodides may be used. The reaction temperature may be varied within a wide range, and preferably is between 20° C. and the boiling point of the solvent.

If desired, the compounds of the formula (I) can be converted into their acid addition salts or quaternary ammonium salts by methods well known in the art. The acid addition salts can be prepared by means of inorganic or organic acids, e.g. hydrogen halides such as hydrochloric acid, hydrogen bromide etc., sulfuric acid, phosphoric acids, formic acid, acetic acid, propionic acid, oxalic acid, glycolic acid, maleic acid, fumaric acid, tartaric acid, succinic acid, ascorbic acid, citric acid, malic acid, salicylic acid, lactic acid, benzoic acid, cinnamic acid, asparaginic acid, glutaminic acid, N-acetyl-asparaginic acid, N-acetyl-glutaminic acid, alkylsulfonic acids such as methanesulfonic acid, arylsulfonic acids such as p-toluene-sulfonic acid, etc.

According to a preferred embodiment the corresponding acid is added to a solution of a compound of the formula (I) in an inert solvent, e.g. ethanol, and the salt formed is precipitated, preferably with a water-immiscible organic solvent such as diethyl ether. Quaternization is preferably carried out with a lower alkyl, alkenyl or benzyl halide or alkyl sulfate. The reaction is performed in an organic solvent, preferably acetone, acetonitrile, ethanol or in a mixture of these solvents, at a temperature between room temperature and the boiling point of the solvent. The quaternary salts can be isolated e.g. by filtration and if desired, are purified by crystallization.

The new compounds of the formula (I) and their salts possess valuable pharmacological properties. More particularly, they can successfully be used in therapy for the treatment of acute ethanolic intoxication. The acute alcoholic intoxication is characterized by euphoria, general stimulation, ataxia, somnolence, paralytic state, etc. The dangers of this toxic, pathologic condition are well known and cannot be neglected, since the intoxicated person exposes his own health to danger and is a threat to his environment (e.g. driving while intoxicated). Alcoholic intoxication is an essential "risk factor" of cerebral ischaemic infarct (Hillbom, M. et al.: Lancet, 2, 1181 (1978); Stroke, 12, 422 (1981)). The ethanolic intoxicated condition has no satisfactory antidote. α-Methyl-para-tyrosine normalizes the ethanolic locomotoric hyperactivity on mice in a dose range, in which a decrease of spontaneous locomotoric activity of the animals is also observed (Carlsson, A. et al.: Psychopharm, 26, 307 (1972)). Various stimulants (caffeine, amphetamine) decrease the narcotizing effect of alcohol but, at the same time, prolong the motoric incoordination (ataxia) (Wallagsen, H. et al.: Actions of alcohol, Amsterdam, Elsevier, 1970; Rech, R. H. et al.: Ann. N.Y. Acad. Sci. 28, 426 (1976); Todzy I. et al.: Psychopharm., 59, 143 (1978)). The alcoholic intoxication, i.e. the narcosis period is shortened by L-cysteine (Sprince, H. et al.: Agents and Actions, 4, 125 (1974); Nagasawa, H. T. et al.: Life Sci., 17, 707 (1975)). This substance is used as a reference in our alcoholic narcosis period tests.

The effect of the compounds according to the invention on ethanolic narcosis period was tested on Hann.-Wistar rats of both sexes, each weighing 160 to 180 g., which were fasted for 16 hours prior to treatment. Groups of 10 were treated with various doses of the test compounds of the formula (I), orally. One hour after treatment, the animals were administered a 3.5 g./kg. dose of ethanol intraperitoneally. The narcosis period of the animals was measured from the elapse of the righting reflex until a spontaneous correction of the body position. The average of the narcosis period for the different groups of animals, the standard error were calculated, and the results are given as a percentage of the control in Table 1.

Abbreviations:
$\bar{x} \pm S.E.$ = mean value ± standard error
n = number of animals The control group was treated with a placebo and a 3.5 g./kg. dose of ethanol.

Narcosis period of the control: $82.6 \pm 8.21$ ($\bar{x} \pm S.E.$) minutes

A = 1-(2-methoxyphenyl)-1-{4-[3-(4-methylpiperazin-1-yl)-propoxy]-phenyl}-propan-1-ol
B = 1-(3-chlorophenyl)-1-{4-[3-(4-benzylpiperazin-1-yl)-propoxy]-phenyl}-propan-1-ol dihydrogen citrate
C = 1-(4-chlorophenyl)-1-{4-[3-(4-methyl-piperazin-1-yl)-propoxy]-phenyl}-propan-1-ol

TABLE 1

| Compound | Dose (mg./kg.) | Ethanolic narcosis period (control ± S.E. %) | —n |
|---|---|---|---|
| A | 40 | 65 ± 8.7 | 10 |
| B | 5 | 53 ± 3.7 | 10 |
|   | 10 | 32 ± 10.1 | 10 |
| C | 40 | 51 ± 8.2 | 10 |
| L-cysteine | 500 | 63 ± 4.7 | 10 |
|   | 1000 | 66 ± 5.9 | 10 |
| Control |   | 100  9.9 | 10 |

As appears from the data given in Table 1, the compounds of the formula (I) essentially shorten the ethanolic narcosis period. While the effect of L-cysteine remained essentially unchanged when increasing its doses up to 1 g./kg., the effect of the compounds provided by the invention is dose-dependent, and is the same or higher than that of L-cysteine in 10 to 100-times smaller doses. In addition, the instant compounds have a favorable acute toxicity. A single 500 mg./kg. oral dose of the compounds was administered to groups of 10 Wistar rats weighing 160 to 180 g. each, and selected from both sexes. The animals were observed for 14 days. There was observed no perish.

The central nervous activities of the compounds according to the invention were examined with the following methods: electroshock (Swinyard, E. A., Brown, W. C., Goodman, L. S.: J. Pharmacol. Exp. Ther. 106, 319 (1952)); metrazole spasm (Everett, G. M., Richards, R. K.: J. Pharmacol. Exp. Ther., 81, 402 (1944)); thiosemicarbazide spasm (Da Vanzo, J. P., Greig, M. E., Cormin, M. A.: Amer. J. Physiol., 201, 833 (1961)); strychnine spasm (Kerley, T. L., Richards, A. G., Begley, R. W., Abreu, B. B., Wesver, L. C.: J. Pharmacol. Exp. Ther., 132, 360 (1961)); nicotine spasm (Stone, C. A., Mecklenburg, K. L., Torhand, M. L.: Arch. Int. Pharmacodyn., 117, 319 (1958)); rotarod test (Kinnard, W. J., Carr, C. J.: J. Pharmacol. Exp. Ther. 121, 354 (1957)); physostigmine lethality preventing effect (Nose, T. and Kojima, M.: Europ. J. Pharmacol. 10, 83 (1970)), yohimbine potentiation effect (Quinton, R. M.: Brit. J. Pharmacol., 21, 51 (1963)); and analgesic activity (Bianchi, C., Franceschini, J.: Brit. J. Pharm. Chemother., 9, 280 (1954)). The compounds showed no central nervous activity when tested with the above methods, even in doses of 160 mg./kg.

The compounds according to the invention antagonize the central nervous activity of alcohol selectively, shorten the time of acute intoxication by 50 to 70%, have a low toxicity and a favorable therapeutic index.

The pharmacologically active compounds according to the invention can be used in therapy in the form of pharmaceutical compositions, which are formulated as preparations suitable for oral, rectal and/or parenteral administration. For oral administration tablets, dragées or capsules are prepared. The oral formulations contain as a vehicle e.g. lactose or starch, as an excipient or a granulation aid e.g. gelatine, carboxymethyl cellulose sodium, methyl cellulose, polyvinyl pyrrolidone or starch gum, as a disintegrating substance e.g. potato starch or microcrystalline cellulose, ultraamylopectin or formaldehyde casein, etc. The formulations may also contain adhesives and lubricants such as talc, colloidal silica, stearine, calcium or magnesium stearate, etc.

Tablets are prepared for example by wet granulation and subsequent pressing. A mixture of the active ingredient and the vehicle and optionally a part of the disintegrating agent are granulated with an aqueous, alcoholic or aqueous-alcoholic solution of the excipients in a suitable equipment, and the granulate is dried. The remaining portion of the disintegrating substance, lubricant, anti-adhesive or optional further additives is then added to the granules, and the mixture is pressed into tablets. If desired, the tablets are prepared with a dividing line which facilitates administration. Tablets can be prepared also from a mixture of the active ingredient and suitable additives by direct pressing.

If desired, the tablets can be converted into dragées, using protecting, flavoring agents and pigments generally known for the preparation of pharmaceutical compositions, e.g. sugar, cellulose derivatives (methyl or ethyl cellulose, carboxymethyl cellulose sodium etc.), polyvinylpyrrolidone, calcium phosphate, calcium carbonate, food pigments, food oil varnishes, aroma substances, iron oxide pigments, etc.

Capsules are prepared by filling a mixture of the active ingredients and additives into suitable capsules.

For rectal administration the compositions are formulated as suppositories which contain in addition to the active ingredient a carrier mass, called adeps pro suppository. Suitable carriers include vegetable fats, e.g. hardened vegetable oils, triglycerides of fatty acids having 12 to 18 carbon atoms, preferably Witepsol (a registered trade mark). The active ingredient is homogenously distributed in the melted carrier mass, and suppositories are prepared by casting.

For parenteral administration injectable preparations are prepared. To prepare an injectable solution the active ingredient is dissolved in distilled water and/or various organic solvents, e.g. glycol ethers, optionally in the presence of dissolution aids, e.g. polyoxyethylene sorbitan monolaurate, monooleate or monostearate (Tween 20, Tween 60, Tween 80). The injectable solutions may contain also various additives, e.g. preserving agents, such as benzyl alcohol, p-oxy-benzoic acid methyl or propyl ester, benzalkonium chloride or phenyl mercuri borate, etc., antioxidants such as ascorbic acid, tocopherol, sodium pyrosulfate and optionally complexing agents to bind metal traces such as ethylene diamine tetraacetate, buffers to adjust the pH and optionally local anaesthetics such as lidocaine. The injectable solutions are filtered, filled into ampoules and sterilized. The daily dose, depending on the state of the patient, varies between 0.1 and 300.0 mg./kg., preferably 2.0 and 160 mg./kg., which is preferably administered in several smaller dose units.

The invention will be further illustrated by the following Examples but it is not intended to limit the scope of the invention to the Examples.

EXAMPLE 1

1-(4-Chlorophenyl)-1-{4-[3-(4-methylpiperazin-1-yl)-propoxy]-phenyl}-propan-1-ol To a Grignard reactant prepared from 2.2 g. of magnesium turnings and 28.2 g. of 4-[3-(4-methylpiperazin-1-yl)-propoxy]-bromobenzene in 170 ml. of dry tetrahydrofurane a solution of 10 g. of p-chloropropiophenone in 30 ml. of tetrahydrofuran is added dropwise at 20° C., and the reaction mixture is stirred for two additional hours. After cooling, the reaction mixture is decomposed with a 20% aqueous ammonium chloride solution. Tetrahydrofurane is distilled off under reduced pressure. The residue is extracted with benzene, the benzene phase is washed to neutral with water, and dried over anhydrous magnesium sulfate. The solvent is distilled off in vacuo, and the residue is crystallized from n-hexane to yield 17.1 g. of the named compounds, melting at 124° to 125° C.

Analysis for $C_{23}H_{31}ClN_2O_2$: Calculated: C 68.55%, H 7.75%, Cl 8.90%, N 6.95%; Found: C 68.63%, H 7.63%, Cl 9.11%, N 6.88%.

A solution of the above base with dry ethanol is treated with a calculated amount of hydrochloric acid in ethanol, and is then diluted with dry ether. The precipitated hydrochloride is filtered off and dried. Melting point: 238° to 239° C.

To the solution of the above base in dry ethanol ethanolic solution of one molar equivalent of citric acid is added. After dilution with dry ether, the crystalline dihydrogen citrate salt is filtered off and dried. Melting point: 87° to 89° C.

EXAMPLE 2

1-(3-Trifluoromethylphenyl)-1-{4-[3-(morpholin-1-yl)-propoxy]-phenyl}-propan-1-ol A mixture of 18.6 g. of 1-(3-trifluoromethylphenyl)-1-[4-(3-chloropropoxy)-phenyl]-propan-1-ol and 26.2 ml. of dry morpholine is refluxed for two hours, under stirring. After cooling morpholine is distilled off from the reaction mixture under reduced pressure. To the residue water and benzene are added. The phases are separated, the benzene phase is washed with water and dried over anhydrous potassium carbonate. Benzene is distilled off in vacuo, and the residue is crystallized from n-hexane to yield 18.2 g. of the named compound, melting at 68° to 70° C.

Analysis for $C_{23}H_{28}F_3NO_3$: Calculated: C 65.23%, H 6.66%, F 13.46%, N 3.31%; Found: C 65.26%, H 6.78%, F 13.54%, N 3.50%.

EXAMPLE 3

1-(4-Fluorophenyl)-1-{4-[3-(4-benzyl-piperazin-1-yl)-propoxy]-phenyl}-propan-1-ol To a Grignard reactant prepared from 2.4 g. of magnesium turnings and 11 g. of ethyl bromide in 40 ml. of dry ether a solution of 10.8 g. of 4-fluoro-4'-[3-(4-benzyl-piperazin-1-yl)-propoxy]-benzophenone in 200 ml. of dry ether is added dropwise, at −30° C. The reaction mixture is stirred at 0° C. for additional 30 minutes, and is then refluxed for one hour. After cooling the reaction mixture is poured onto a solution of ammonium chloride in ice water. The ethereal phase is separated. The aqueous phase is extracted with ether. The ethereal phases are combined and washed to neutral with water. After drying over anhydrous magnesium sulfate, the solution is evaporated in vacuo. The residue is crystallized from isopropyl ether. 5.3 g. of the end product are obtained, melting at 119° to 121° C.

Analysis for $C_{29}H_{35}FN_2O_2$: Calculated: C 75.29%, H 7.63%, F 4.11%, N 6.06%; Found: C 75.35%, H 7.67%, F 4.30%, N 6.17%.

EXAMPLE 4

1-(3-Chlorophenyl)-1-{4-[3-(4-benzyl-piperazin-1-yl)-propoxy]-phenyl}-propan-1-ol To a Grignard reactant prepared from 2.5 g. of magnesium turnings and 19.1 g. of 3-chloro-bromobenzene in 80 ml. of tetrahydrofuran a solution of 25.6 g. of 4-[3-(4-benzyl-piperazin-1-yl)-propoxy]-propiophenone in 55 ml. of dry tetrahydrofuran is added dropwise, under slight reflux. The reaction mixture is slightly boiled for another two hours. After cooling the reaction mixture is poured onto a solution of ammonium chloride in ice water. The phases are separated, and the aqueous phase is extracted with tetrahydrofuran. The tetrahydrofuran phases are combined, washed to neutral with a saturated, aqueous sodium chloride solution and dried over anhydrous potassium carbonate. The solvent is distilled off under reduced pressure. The residue is fractionated in vacuo. 20.1 g. of the named compound are obtained, boiling at 252° to 254° C. (6.6 Pa).

Analysis for $C_{29}H_{35}ClN_2O_2$: Calculated: C 72.70%, H 7.36%, Cl 7.40%, N 5.85%; Found: C 72.74%, H 7.55%, Cl 7.28%, N 5.91%.

Melting point of the corresponding dihydrogen citrate: 67° to 69° C.

EXAMPLE 5

1-(3-Trifluoromethylphenyl)-1-{4-[3-(4-methylpiperazin-1-yl)-propoxy]-phenyl}-propan-1-ol To 200 ml. of a 0.5 molar ethereal 3-trifluoromethylphenyl lithium solution a solution of 8.7 g. of 4-[3-(4-methyl-piperazin-1-yl)-propoxy]-propiophenone in 270 ml. of dry ether is added dropwise, in argon atmosphere, at −30° C. The reaction mixture is then stirred for further 3 hours. It is decomposed with a 20% aqueous ammonium chloride solution, the aqueous phase is extracted with ether, the etheral phases are combined and washed to neutral with water. The organic phase is dried over anhydrous magnesium sulfate, and ether is distilled off in vacuo. The residue is crystallized from a mixture of n-hexane and benzene, to yield 3.6 g. of the aimed product, melting at 129° to 130° C.

Analysis for $C_{24}H_{31}F_3N_2O_2$: Calculated: C 66.03%, H 7.16%, F 13.06%, N 6.42%; Found: C 66.15%, H 7.32%, F 13.00%, N 6.34%.

EXAMPLE 6

1-(2-Methoxyphenyl)-1-{4-[3-(4-methyl-piperazin-1-yl)-propoxy]-phenyl}-propan-1-ol 12.9 g. of 1-(2-methoxyphenyl)-1-(4-hydroxyphenyl)-propan-1-ol, 14 g. of anhydrous potassium carbonate, 9.7 g. of 3-(4-methyl-piperazin-1-yl)-propyl chloride and 0.85 g. of tetrabutylammonium bisulfate in 140 ml. of ethyl acetate are refluxed for 20 hours, under stirring. After cooling the mixture, the solvent is distilled off under reduced pressure. To the residue water is added, and it is extracted with benzene. The benzene phase is washed with water, and dried over anhydrous magnesium sulfate. The solvent is distilled off in vacuo, and the residue is crystallized from n-hexane to yield 14.5 g. of the named compounds, melting at 112° to 113° C.

Analysis for $C_{24}H_{34}N_2O_3$: Calculated: C 72.32%, H 8.60%, N 7.03%; Found: C 72.27%, H 8.73%, N 7.15%.

Melting point of the corresponding dihydrogen citrate: 105° to 107° C.

EXAMPLE 7

1-(4-Chlorophenyl)-1-{4-[3-(4-benzyl-piperazin-1-yl)-propoxy]-phenyl}-propan-1-ol 6.6 g. of 1-(4-chlorphenyl)-1-(4-hydroxyphenyl)-propan-1-ol, 11.5 g. of anhydrous potassium carbonate, 0.2 ml. of a 40% tetrabutyl ammonium hydroxide solution, 6.3 g. of 3-(4-benzyl-piperazin-1-yl)-propyl chloride and 70 ml. of methyl ethyl ketone are boiled for 4 hours. The solvent is distilled off under reduced pressure, to the residue benzene and water are added. The benzene phase is washed to neutral with water, dried over anhydrous potassium carbonate, and benzene is distilled off in vacuo. The residue is taken up in dry ethanol, and treated with an ethanolic solution of 2.85 g. of fumaric acid. The precipitated hydrogen fumarate salt is filtered off, crystallized from a mixture of methanol and dimethyl formamide. 11.2 g. of the monohydrogen fumarate of the named base are obtained, melting at 205° to 207° C. The corresponding base is set free with ammonium hydroxide.

Analysis for $C_{29}H_{35}ClN_2O_2$: Calculated: C 72.70%, H 7.36%, Cl 7.40%, N 5.85%; Found: C 72.66%, H 7.33%, Cl 7.58%, N 5.91%.

EXAMPLE 8

1-(4-Chlorophenyl)-1-{4-[3-(4-methyl-piperazin-1-yl)-propoxy]-phenyl}-propan-1-ol dimethoiodide A mixture of 4 g. of the corresponding base, 20 ml. of acetone and 5.6 g. of methyl iodide is slightly refluxed for one hour, whereupon the mixture is allowed to stand under cooling. The precipitated crystals are filtered off, and rectystallized from 95% ethanol. 5.1 g. of the above quaternary compound are obtained, melting at 186° to 188° C.

1-(2-Methoxyphenyl)-1-{4-[3-(4-methylpiperazin-1-yl)-propoxy]-phenyl}-propan-1-ol dimethoiodide can be prepared by an analogous reaction from the corresponding base. Melting point: 228° to 230° C. (decomp.).

The following compounds can be prepared essentially following the procedures disclosed in Examples 1 to 7, by proper selection of the starting substances.

1-(3-Chlorophenyl)-1-{4-[3-(4-methyl-piperazin-1-yl)-propoxy]-phenyl}-propan-1-ol,
melting point: 110° to 111° C.

Analysis for $C_{23}H_{21}ClN_2O_2$: Calculated: C 68.55%, H 7.75%, Cl 8.80%, N 6.95%; Found: C 68.66%, H 7.82%, Cl 8.88%, N 7.13%.

1-(2-Methoxyphenyl)-1-{4-[3-(4-benzyl-piperazin-1-yl)-propoxy]-phenyl}-propan-1-ol,
melting point: 63° to 64° C.

Analysis for $C_{30}H_{38}N_2O_3$: Calculated: C 75.91%, H 8.07%, N 5.90%; Found: C 75.84%, H 8.14%, N 6.11%.

1-(2-Methoxyphenyl)-1-{4-[3-(2-methyl-imidazol-1-yl)-propoxy]-phenyl}-propan-1-ol,
melting point: 90° to 91° C.

Analysis for $C_{23}H_{28}N_2O_3$: Calculated: C 72.60%, H 7.42%, N 7.36%; Found: C 72.55%, H 7.61%, N 7.55%.

1-(2-Methoxyphenyl)-1-{4-[3-(imidazol-1-yl)-propoxy]-phenyl}-propan-1-ol,
melting point: 67° to 68° C.

Analysis for $C_{22}H_{26}N_2O_3$: Calculated: C 72.10%, H 7.15%, N 7.64%; Found: C 72.17%, H 7.28%, N 7.71%.

1-(3-Trifluoromethylphenyl)-1-{4-[3-(N-methyl-N-cyclohexylamino)-propoxy]-phenyl}-propan-1-ol,
melting point: 75° to 76° C.

Analysis for $C_{26}H_{34}F_3NO_2$: Calculated: C 69.46%, H 7.62%, F 12.68%, N 3.12%; Found: C 69.60%, H 7.69%, F 12.85%, N 3.23%.

EXAMPLE 9

The new compounds according to the invention can for example be converted into the following pharmaceutical compositions.

| Tablets | |
|---|---|
| Compositions of a single tablet: | |
| active ingredient | 100.0 mg. |
| lactose | 184.0 mg. |
| potato starch | 80.0 mg. |
| polyvinyl pyrrolidone | 8.0 mg. |
| talc | 12.0 mg. |
| magnesium stearate | 2.0 mg. |
| aerosil (colloidal $SiO_2$) | 2.0 mg. |
| ultraamylopectin | 12.0 mg. |

From the above ingredients 400-mg. tablets are prepared by wet granulation and subsequent pressing.

Active ingredient: 1-(3-chlorophenyl)-1-{4-[3-(4-benzyl-piperazin-1-yl)-propoxy]-phenyl}-propan-1-ol dihydrogen citrate

DRAGÉES

Tablets as described above are coated with a layer prepared from sugar and talc in a known manner. Dragées are polished with a mixture of bee wax and carnauba wax. Weight of a dragée: 500.0 mg.

| Capsules | |
|---|---|
| Composition of a single capsule: | |
| active ingredient | 50.0 mg. |
| lactose | 100.0 mg. |
| talc | 2.0 mg. |
| potato starch | 30.0 mg. |
| cellulose (microcrystalline) | 8.0 mg. |

The active ingredient is thoroughly admixed with the additives, the mixture is passed through a 0.32-mm. sieve, and filled into hard gelatine capsules (size 4).

Active ingredient: 1-(4-chlorophenyl)-1-{4-[3-(4-methyl-piperazin-1-yl)-propoxy]-phenyl}-propan-1-ol

| Suppositories | |
|---|---|
| Composition of a suppository: | |
| active ingredient | 100.0 mg. |
| lactose | 200.0 mg. |
| basic substance (e.g. Witepsol H) | 1700.0 mg. |

The basic substance is melted and then cooled to 35° C. The active ingredient is thoroughly blended with the lactose, and the mixture is homogenized in the basic substance with a homogenizator. The obtained mass is poured into cool mold. One suppository weights 2000 mg.

Active ingredient: 1-(3-chlorophenyl)-1-{4-[3-(4-benzyl-piperazin-1-yl)-propoxy]-phenyl}-propan-1-ol

| Suspension | |
|---|---|
| Composition of 100 ml. of suspension: | |
| active ingredient | 1.0 g. |
| sodium hydroxide | 0.26 g. |
| citric acid | 0.30 g. |
| nipagin (4-hydroxybenzoic acid methylester sodium salt) | 0.10 g. |
| Carbopol 940 (polyacrylic acid) | 0.30 g. |
| ethanol (96%) | 1.00 g. |
| raspberry aroma | 0.60 g. |
| sorbitol (70% aqueous solution) | 71.00 g. |
| distilled water | ad 100.00 ml. |

To a solution of nipagin and citric acid in 20 ml. of distilled water Carbopol is added portionwise, with vigorous stirring, and the solution is allowed to stand for 10 to 12 hours. Thereafter a solution of the above amount of sodium hydroxide in 1 ml. of distilled water is added dropwise, followed by dropwise addition of an aqueous solution of sorbitol and an ethanolic raspberry aroma solution, under stirring. Active ingredient is added in small portions, and the mixture is homogenized. The suspension is supplemented with distilled water ad 100 ml., and the suspension syrup is passed through a colloid mill.

Active ingredient: 1-(2-methoxyphenyl-1-{4-[3-(4-methyl-piperazin-1-yl)-propoxy]-phenyl}-propan-1-ol.

We claim:

1. A compound of the Formula (I)

$$\text{(I)}$$

(structure: a biphenyl-like compound with two phenyl rings connected through a central carbon bearing OH and $C_2H_5$; one ring bears $R_1$, the other bears $-O-CH_2-CH_2-CH_2-N(R_2)(R_3)$)

wherein
$R_1$ is halogen, trihalomethyl, or alkoxy having 1 to 3 carbon atoms; and
$R_2$ and $R_3$ together with the nitrogen atom to which they are attached form a piperazino group which can be substituted in the 4-position by $C_1$ to $C_4$ alkyl or benzyl; or a pharmaceutically acceptable acid addition or quaternary ammonium salt thereof.

2. A compound of the Formula (I)

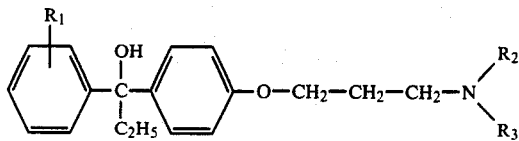

wherein

R₁ is halogen, trihalomethyl, or alkoxy having 1 to 3 carbon atoms; and

R₂ and R₃ together with the nitrogen atom to which they are attached form a 4-methyl-piperazinyl or a 4-benzyl-piperazinyl group; or a pharmaceutically acceptable acid addition or quaternary ammonium salt thereof.

3. The compound of the Formula (I) defined in claim 1 which is selected from the group consisting of:

1-(2-methoxyphenyl)-1-(4-[3-(4-methyl-piperazin-1-yl)-propoxy]-phenyl)-propan-1-ol;

1-(3-chlorophenyl)-1-(4-[3-(4-benzyl-piperazin-1-yl)-propoxy]-phenyl)-propan-1-ol; and 1-(4-chlorophenyl)1-(4-[3-(4-methyl-piperazin-1-yl)-propoxy]-phenyl)-propan-1-ol; or a pharmaceutically acceptable acid addition or quaternary ammonium salt thereof.

4. A pharmaceutical composition for the treatment of ethanolic intoxication which comprises a pharmaceutically effective amount of the compound of the Formula (I) as defined in claim 1 or a pharmaceutically acceptable acid addition or quaternary ammonium salt thereof, in combination with a pharmaceutically acceptable inert carrier.

5. A method of treating ethanolic intoxication in an affected animal subject which comprises administering a pharmaceutically effective amount of the compound of the Formula (I) as defined in claim 1 or a pharmaceutically acceptable acid addition or quaternary ammonium salt thereof to said subject.

* * * * *